United States Patent [19]

Strickler et al.

[11] Patent Number: 5,847,175
[45] Date of Patent: *Dec. 8, 1998

[54] ENHANCED SYNTHESIS OF RACEMIC METALLOCENES

[75] Inventors: Jamie R. Strickler; John M. Power, both of Baton Rouge, La.

[73] Assignee: Albemarle Corporation, Richmond, Va.

[ * ] Notice: The term of this patent shall not extend beyond the expiration date of Pat. No. 5,556,997.

[21] Appl. No.: 833,110

[22] Filed: Apr. 4, 1997

Related U.S. Application Data

[63] Continuation-in-part of Ser. No. 427,505, Apr. 25, 1995, Pat. No. 5,556,997.

[51] Int. Cl.$^6$ .............................. C07F 17/00; C07F 19/00; C07F 7/00
[52] U.S. Cl. .................................. 556/11; 556/1; 556/12; 556/43; 556/47; 556/53; 534/15; 502/103; 502/117; 526/943
[58] Field of Search ..................................... 556/1, 11, 12, 556/43, 47, 53; 534/15; 526/943; 502/103, 117

[56] References Cited

FOREIGN PATENT DOCUMENTS

| | | |
|---|---|---|
| 2055218 | 5/1992 | Canada . |
| 0530908 | 3/1993 | European Pat. Off. . |
| 0581754 | 2/1994 | European Pat. Off. . |

OTHER PUBLICATIONS

Ray, T.C., et al., Inorg. Chem., (1965), pp. 1501–1504.

Spaleck, Walter, et al., Angew, Chem. Int. Ed., (1992), vol. 31, pp. 1347–1350.

Spaleck, Walter, et al., Organometallics, (1994), vol. 13, pp. 954–963.

*Primary Examiner*—Porfirio Nazario-Gonzalez
*Attorney, Agent, or Firm*—Philip M. Pippenger

[57] ABSTRACT

Chiral metallocenes are prepared by reacting a salt of an asymmetric bis(cyclopentadienyl)-moiety-containing ligand with a chelate diamine adduct of a transition, lanthanide, or actinide metal halide in an organic solvent or diluent so as to produce said chiral metallocene.

23 Claims, No Drawings

ENHANCED SYNTHESIS OF RACEMIC METALLOCENES

This application is a continuation-in-part of copending International Application PCT/US 96/05089 having an International filing date of Apr. 12, 1996 and designating, inter alia, the United States of America, the aforesaid International Application claiming priority from earlier U.S. application Ser. No. 427,505, filed Apr. 24, 1995, now U.S. Pat. No. 5,556,997, issued Sep. 17, 1996, and the aforesaid International Application to be treated as in the United States of America as a continuation-in-part of said U.S. application Ser. No. 427,505.

The invention relates generally to the preparation of metallocenes which are useful as stereoregular olefin polymerization catalysts and more specifically to a process for metallizing cyclopentadienyl ligand salts with certain transition, lanthanide or actinide metal compounds which are chelate diamine adducts of the metal halides.

As known in the art, metallocenes can be prepared by reacting a metal compound of the formula $MX_n$, where M is the metal, n is an integer of 1 to 6, depending upon the valence of M, and X is independently an anionic ligand group or a neutral Lewis base ligand group having up to 30 non-hydrogen atoms such as hydride, halo, alkyl, aryl, silyl, germyl, aryloxy, alkoxy, amide, and siloxy, with an alkali metal or a magnesium halide salt of a cyclopentadienyl ligand in a solvent such as an ether.

Chiral metallocenes are useful for the synthesis of polyolefins. Specifically, the racemic form of the metallocene provides stereoregular poly(alpha-olefins) in addition to being considerably more active than the meso form, which produces only atactic polymers. An efficient synthesis of chiral metallocenes that favors the formation of the racemic isomer at the metallation stage is desired. We have now found that by using certain chelate diamine adducts of a metal halide in the reaction with the salt of the cyclopentadienyl ligand, enhanced formation of the racemic isomer and/or better product yields can be produced, especially by using a mixed ether-hydrocarbon reaction solvent or diluent and/or by preparing the adduct at elevated temperatures.

In accordance with this invention there is provided a process for preparing a chiral metallocene, said process comprising reacting a salt of an asymmetric bis(cyclopentadienyl) moiety containing ligand with a chelate diamine adduct of a transition, lanthanide or actinide metal halide in an organic solvent or diluent so as to produce said chiral metallocene.

Chiral metallocenes which can be prepared in accordance with the process of the invention preferably contain a metal from Groups 3–10, or the lanthanide and actinide series of the Periodic Table of the elements and, more preferably a Group 4 to 6 transition metal, which is coordinated with a ligand containing a pair of cyclopentadienyl moieties, at least one of which is asymmetric, which moieties are stereorigid such as by being joined by a bridging group. The cyclopentadienyl moieties can be substituted with one or more groups, such as halogen, amino, mercapto, phosphino, and $C_1$ to $C_{20}$ hydrocarbyl, silahydrocarbyl, or halohydrocarbyl and the like and can include moieties which are condensed, multi-ring structures such as, for example, indenyl, benzoindenyl, or fluorenyl, which structures can be hydrogenated and/or further substituted. The other groups on the metal atom usually include hydride, halogen, hydrocarbyl or halohydrocarbyl having up to about 6 carbons. Such chiral metallocenes, and their use as catalysts in forming isotactic olefin polymers are described, for example, in U.S. Pat. Nos. 5,017,714; 5,036,034; 5,145,819; 5,296,434; 5,324,800 and 5,329,033, whose disclosures are incorporated herein by reference. Typical bridging groups include silicon containing bridges of 1–4 atoms selected from silanylene, silaalkylene, oxasilanylene and oxasilaalkylene, such as, dimethylsilanylene. The chiral metallocenes are mixtures of racemic diasteriomers which have no plane of symmetry. In contrast, the meso isomers have a plane of symmetry running through the metal between the rings and are, therefore achiral.

Specific, non-limiting examples of chiral metallocenes include racemic:
[1,1'-dimethylsilanylenebis(3-methylcyclopentadienyl)] zirconium dichloride;
[1,1'-dimethylsilanylenebisindenyl]zirconium dichloride;
[1,1'-dimethylsilanylenebis(4,5,6,7-tetrahydroindenyl)] zirconium dichloride;
[1,1'-(1,1,2,2-tetramethyldisilanylene)bis(3-methylcyclopentadienyl)]zirconium dichloride;
[1,1'-(1,1,2,2-tetramethyldisilanylene)bis(4,5,6,7-tetrahydroindenyl)]zirconium dichloride;
[1,1'-dimethylsilanylenebis(3-trimethylsilanylcyclopentadienyl)]zirconium dichloride;
[1,1'-(1,1,2,2-tetramethyldisilanylene)bis(3-trimethylsilanylcyclopentadienyl)]zirconium dichloride;
[1,1'-(1,1,3,3-tetramethyldisilanylene)bis(4,5,6,7-tetrahydroindenyl)]zirconium dichloride;
[1,1'-(1,1,4,4-tetramethyl-1,4-disilanylbutylene)bis(4,5,6,7-tetrahydroindenyl)]zirconium dichloride;
[1,1'-(2,2-dimethyl-2-silapropylene)bis(3-methylcyclopentadienyl)]zirconium dichloride;
[1,1'-dimethylsilanylenebis(3-methylcyclopentadienyl)] titanium dichloride;
[1,1'-dimethylsilanylenebisindenyl]titanium dichloride;
[1,1'-dimethylsilanylenebis(4,5,6,7-tetrahydroindenyl)] titanium dichloride;
[1,1'-(1,1,2,2-tetramethyldisilanylene)bis(3-methylcyclopentadienyl)]titanium dichloride;
[1,1'-(1,1,2,2-tetramethyldisilanylene)bis(4,5,6,7-tetrahydroindenyl)]titanium dichloride;
[1,1'-dimethylsilanylenebis(3-trimethylsilanylcyclopentadienyl)]titanium dichloride;
[1,1'-(1,1,2,2-tetramethyldisilanylene)bis(3-trimethylsilanylcyclopentadienyl)]titanium dichloride;
[1,1'-(1,1,3,3-tetramethyldisilanylene)bis(4,5,6,7-tetrahydroindenyl)]titanium dichloride;
[1,1'-(1,1,4,4-tetramethyl-1,4-disilanylbutylene)bis(4,5,6,7-tetrahydroindenyl)]titanium dichloride;
[1,1'-(2,2-dimethyl-2-silapropylene)bis(3-methylcyclopentadienyl)]titanium dichloride;
[1,1'-dimethylsilanylenebis(3-methylcyclopentadienyl)] hafnium dichloride;
[1,1'-dimethylsilanylenebisindenyl]hafnium dichloride;
[1,1'-dimethylsilanylenebis(4,5,6,7-tetrahydroindenyl)] hafnium dichloride;
[1,1'-(1,1,2,2-tetramethyldisilanylene)bis(3-methylcyclopentadienyl)]hafnium dichloride;
[1,1'-(1,1,2,2-tetramethyldisilanylene)bis(4,5,6,7-tetrahydroindenyl)]hafnium dichloride;
[1,1'-dimethylsilanylenebis(3-trimethylsilanylcyclopentadienyl)]hafnium dichloride;
[1,1'-(1,1,2,2-tetramethyldisilanylene)bis(3-trimethylsilanylcyclopentadienyl)]hafnium dichloride;
[1,1'-(1,1,3,3-tetramethyldisilanylene)bis(4,5,6,7-tetrahydroindenyl)]hafnium dichloride;
[1,1'-(1,1,4,4-tetramethyl-1,4-disilanylbutylene)bis(4,5,6,7-tetrahydroindenyl)]hafnium dichloride;

[1,1'-(2,2-dimethyl-2-silapropylene)bis(3-methylcyclopentadienyl)]hafnium dichloride;
dimethylsilylbis(1-(2-methyl-4-ethylindenyl))zirconium dichloride;
dimethylsilylbis(1-(2-methyl-4-isopropylindenyl)) zirconium dichloride;
dimethylsilylbis(1-(2-methyl-4-tert-butylindenyl)) zirconium dichloride;
methylphenylsilylbis(1-(2-methyl-4-isopropylindenyl)) zirconium dichloride;
dimethylsilylbis(1-(2-ethyl-4-methylindenyl))zirconium dichloride;
dimethylsilylbis(1-(2,4-dimethylindenyl))zirconium dichloride;
dimethylsilylbis(1-(2-methyl-4-ethylindenyl))zirconium dimethyl;
dimethylsilyl(2-methyl-4,5,6,7-tetrahydro-1-indenyl)) zirconium dichloride;
dimethylsilylbis(2-methyl-4,5-benzoindenyl)zirconium dichloride;
ethylene(2-methyl-4,5,6,7-tetrahydro-1-indenyl)$_2$ zirconium dichloride;
dimethylsilyl(2-methyl-4,5,6,7-tetrahydro-1-indenyl)$_2$ dimethyl zirconium;
phenyl(methyl)silyl(indenyl)$_2$zirconium dichloride;
dimethylsilyl (2,3,5-trimethyl-1-cyclopentadienyl)$_2$ zirconium dichloride;
dimethylgermyl(indenyl)$_2$zirconium dichloride;
ethylene(indenyl)$_2$zirconium dichloride;
methylene(3-t-butyl-1-cyclopentadienyl)$_2$zirconium dichloride;
dimethylsilyl(4,7-dimethyl-1-indenyl)$_2$zirconium dichloride;
dimethylsilanylbisindenylthorium dichloride; and
dimethylsilanylbisindenyluranium dichloride.

The metallocenes are prepared by first deprotonating the appropriate ligand compound using an alkali metal, an alkali metal salt, a magnesium salt or a Grignard reagent to form an alkali metal, magnesium or magnesium halide salt of the ligand. Examples of deprotonizing agents include Na powder, RLi, NaH, LiH and RMgX, where R is $C_1$ to $C_{10}$ hydrocarbyl and X is halogen. Preferred are alkyllithium compounds such as methyllithium, n-butyllithium, s-butyllithium, t-butyllithium, phenyllithium and the like.

Suitable reaction solvents are aliphatic or aromatic hydrocarbon or halocarbon solvents and acyclic or cyclic ethers. Mixed ether and hydrocarbon or halohydrocarbon solvents in ratios of from about 9:1 to 1:9 by volume ether to hydrocarbon solvent and, preferably, 4:1 to 1:2 provide improved yields of the metallocenes having increased racemic isomer content. Examples of suitable solvents include diethyl ether, tetrahydrofuran (THF), ethylene glycol dimethyl ether, hexanes, cyclohexane, heptane, pentane, toluene, benzene, xylene, chlorobenzene and the like. Mixtures of THF and toluene have provided good yields of racemic isomer enriched product, especially in the case of zirconium metallocenes.

The ligand salt, such as the dilithium salt, from the deprotonation is reacted with a chelate diamine adduct of a transition, lanthanide or actinide metal compound and, preferably a metal halide, in order to form the racemic metallocene. Suitable diamines for forming the adducts which are effective to provide metallocenes with an enhanced yield of racemic isomer, include tertiary diamines and especially N,N,N'N'-tetramethylethylenediamine (TMEDA) and tetramethyldiaminomethane (TMDAM). A metal chloride to diamine ratio of 1:0.5 to 1:5 provides improved yields of the racemic metallocene. About equimolar to about a 10% excess of diamine is preferably used. Preferably, the diamine adduct of the metal is formed prior to mixing it with the ligand.

Non-limiting examples of transition, lanthanide and actinide metals include Ti, Zr, Hf, V, Cr, La, Ce, Th, U and the like. Preferred for catalyst use are the Group 4 metals Ti, Zr and Hf.

The adducts can be prepared in hydrocarbon solvents such as those named above for the deprotonation reaction and, preferably toluene, and either separated from the solvent, such as by filtration, or the adduct in solvent can be used in situ for metallation.

It was found pursuant to this invention that the yields of metallocene product could be improved by preparing the adduct at elevated temperature, e.g. about 40° to 110° C. NMR indicates that the composition of the adduct is different as compared with adducts prepared at ambient temperatures.

In addition, it was found that in carrying out the metallation reaction, a mixed hydrocarbon/ether solvent (toluene/THF) reaction medium gave higher yields of enhanced rac/meso isomer ratio product, as compared to previously used solvent systems. The metallation reaction temperature is not critical and can range from about −20° to 120° C. and, preferably, from about 0° to 60° C. Stoichiometric to about a 10% excess amount of metal adduct to ligand salt is preferably used. It was also found that adding a small amount of metallocene product (preferably, amounts which are about 0.05 to 5 wt. % of the metal adduct) and/or ether solvent (THF) (preferably amounts which are about 1 to 20 wt. % based on total solvent) to the adduct slurry prior to the metallation reaction further enhances yields and reproducibility which lowers costs by reducing the cycle time. The filterability of the product mixture also improved and can be further enhanced by adding a non-polar solvent such as a paraffin (hexane) to the solution.

It has now been found that it is possible to achieve even better results by mixing together (i) a solution of a salt of an asymmetric bis(cyclopentadienyl)-moiety-containing ligand (in whatever chemical form it exists while in such solution), to (ii) an organic liquid medium containing a solution or slurry of a chelate diamine adduct of a transition, lanthanide or actinide metal halide (in whatever chemical form it exists while in such solution or slurry), at least 50 weight percent of the liquid solvent of the solution of (i) being one or more liquid aliphatic or cycloaliphatic polyethers, and at least 50 weight percent of the liquid solvent or diluent of the solution or slurry of (ii) being one or more liquid aliphatic, cycloaliphatic or aromatic hydrocarbons. Preferably, the balance, if any, of the liquid solvent of the solution of (i) is composed of one or more liquid hydrocarbons, which can be aliphatic, cycloaliphatic and/or aromatic hydrocarbons. Examples of such polyethers include 1-ethoxy-2-methoxyethane, 1,2-diethoxyethane, 1-tert-butoxy-2-ethoxyethane, 1-tert-butoxy-2-methoxyethane, dimethyl ether of diethylene glycol, diethyl ether of diethylene glycol, tert-butyl methyl ether of diethylene glycol, dimethyl ether of triethylene glycol, 1,3-dioxolane, 2-methyl-1,3-dioxolane, 1,3-dioxane, and like liquid hydrocarbyl polyethers. As between the aliphatic and cycloaliphatic polyethers, the aliphatic polyethers are more preferred and of the latter, 1,2-dimethoxyethane (glyme) is especially preferred. The salt of the asymmetric bis(cyclopentadienyl)-moiety-containing ligand can be preformed and added to or otherwise blended with the one or more polyethers being used, or the asymmetric bis(cyclopentadienyl)-moietycontaining ligand can be formed in situ in such polyether or polyethers being used. Likewise before, during and/or after forming some of the asymmetric bis(cyclopentadienyl)-moiety-containing ligand in situ in the polyether or polyethers being used, additional preformed asymmetric bis (cyclopentadienyl)-moiety-containing ligand can be added to or otherwise blended with the polyether or the partially formed ligand solution.

By the same token, the balance, if any, of the liquid solvent or diluent of the solution or slurry of (ii) in the immediately preceding paragraph is composed of one or more liquid aliphatic and/or cycloaliphatic hydrocarbons, or one or more liquid ethers and/or polyethers, or mixtures of one or more such hydrocarbons and one or more such ethers, and even more preferably the solvent or diluent used in the formation of the solution or slurry of (ii) is essentially entirely one or more such liquid hydrocarbons. Examples of such hydrocarbons include one of more of the liquid hexanes, heptanes, octanes, nonanes, decanes, undecanes, dodecanes, cyclohexane, methylcyclohexane, one or more liquid dimethylcyclohexanes, benzene, toluene, one or more of the xylenes, ethylbenzene, propylbenzene, one or more of the diethylbenzenes, butylbenzene, pentylbenzene, tetrahydronaphthalene, and similar liquid paraffinic, cycloparaffinic or aromatic hydrocarbons, and mixtures of any such substances including gasoline fractions, BTX, petroleum ethers, and the like. The aromatic hydrocarbons are preferred for this use, and of these the mononuclear aromatic hydrocarbons having from 6 to about 8 carbon atoms are more preferred. Toluene is particularly preferred. The chelate diamine adduct of the transition, lanthanide or actinide metal halide can be preformed and added to or otherwise blended with the one or more hydrocarbons being used, or the adduct can be formed in situ in such hydrocarbon or hydrocarbons being used. Likewise before, during and/or after forming some of the adduct in situ in the hydrocarbon (s) being used, additional preformed adduct can be added to or otherwise blended with the hydrocarbon(s) or the partially formed adduct solution or slurry.

Preferably, the solution of (i)—i.e., the above ligand solution—is added to the solution or slurry of (ii)—i.e., the above adduct solution or slurry. This embodiment of the invention is applicable to synthesis of chiral bridged metallocenes of transition, lanthanide and actinide metal halides in general, and preferably is used in connection with reactions with halides (preferably chlorides or bromides) of Group 4–6 metals, and especially in connection with formation of chiral bridged zirconium and hafnium metallocenes.

The invention is further illustrated by, but is not intended to be limited to, the following examples.

Example 1a $ZrCl_4$ (61.9 grams, 0.266 mol) was slurried in 400 mL of anhydrous toluene. N,N,N',N'-tetramethylethylenediamine (TMEDA) (31.74 grams, 0.273 mol) was added dropwise over 20 minutes. The slurry was stirred overnight and then filtered on a coarse frit. The solids were washed with 50 mL of toluene and dried in vacuo. The yield of $ZrCl_4$(TMEDA) was 88.2 grams (95%).

Example 1b $ZrCl_4$(TMEDA) (35.56 g; 0.102 mol) from Example 1a was placed in a 1 L flask with 260 mL of THF. Most of the solids dissolved. After cooling this material to 0° C., a THF solution of dilithium salt of dimethylsilylbis(2-methylindene)($Et_2O$) (40.93 grams, 0.102 mol; 300 mL THF) was added dropwise over 3.5 hours. An orange solid precipitated. The reaction was warmed to ambient temperature and stirred overnight. The orange solids were then filtered on a coarse frit, washed with 25 mL of THF, and dried in vacuo. The yield of crude dimethylsilylbis(2-methylindenyl)zirconium dichloride product was 12.24 grams (26%). This solid was extracted with 700 mL of methylene chloride, filtered through a medium frit, and stripped nearly to dryness. Hexanes were added (100 mL) to precipitate the dissolved product. The recrystallized product was filtered on a coarse frit. The purified yield was 8.59 grams (18%). $^1$H NMR in $CDCl_3$ revealed a pure product composed of 93% racemic and 7% meso diasteriomers.

Example 2

$ZrCl_4$ (2.26 grams, 0.00970 mol) was slurried in 20 mL of anhydrous toluene. TMEDA (1.23 g, 0.0106 mol) was added dropwise. The slurry was stirred for 17 hours. Di-lithium salt of dimethylsilylbis(2-methylindene)($Et_2O$) (3.87 grams, 0.00961 mol) was dissolved in 27 mL of anhydrous THF and added dropwise to the zirconium slurry over approximately ten minutes. The solution cleared briefly during the addition and then an orange solid precipitated. The reaction was stirred overnight. The orange solids were then filtered on a medium frit, washed with 10 mL of toluene, and dried in vacuo. The yield of crude dimethylsilylbis(2-methylindenyl) zirconium dichloride product was 2.75 grams (60%). After extracting this material into methylene chloride, the purified yield was determined to be 55%. A $^1$H NMR spectrum in $CDCl_3$ showed pure product composed of 93% racemic and 7% meso diasteriomers of dimethylsilylbis(2-methylindenyl)zirconium dichloride product.

Example 3

$ZrCl_4$ (2.24 grams, 0.00961 mol) was slurried in 20 mL of anhydrous toluene. TMEDA (1.23 grams, 0.0106 mol) was added dropwise. After less than five minutes, dilithium salt of dimethylsilylbis(2-methylindene)($Et_2O$) (3.86 grams, 0.00959 mol) in 27 mL of anhydrous THF was added dropwise to the zirconium slurry over approximately fifteen minutes. The solution cleared briefly during the addition and then an orange solid precipitated. The reaction was stirred overnight. The orange solids were then filtered on a medium frit, washed with 10 mL of toluene, and dried in vacuo. The yield of crude dimethylsilylbis(2-methylindenyl)zirconium dichloride product was 2.51 grams (55%). After extracting this material into methylene chloride, the purified yield was determined to be 47.5%. A $^1$H NMR spectrum in $CDCl_3$ showed pure product composed of 93% racemic and 7% meso diasteriomers.

Example 4

$ZrCl_4$ (2.95 grams, 0.0127 mol) was slurried in 30 mL of anhydrous toluene. Tetramethyldiaminomethane (TMDAM) (1.42 grams, 0.00139 mol) was added dropwise to the slurry. The slurry was stirred overnight. Dilithium salt of dimethylsilylbis(2-methylindene)($Et_2O$) (5.112 grams, 0.0127 mol) dissolved in 35 mL of anhydrous THF was added dropwise to the zirconium slurry at ambient temperature. The solution cleared briefly during the addition and then an orange solid precipitated. The reaction was stirred overnight. The orange solids were isolated on a coarse frit, washed with toluene, and dried in vacuo. The yield of crude dimethylsilylbis(2-methylindenyl)zirconium dichloride product was 3.43 grams (57%). A $^1$H NMR in $CDCl_3$ showed the product to be of similar purity to the crude product of Example 2.

Comparison Example 1

$ZrCl_4(THF)_2$ (2.17 g; 0.00575 mol) was placed in a 100 mL Schlenk flask with 15 mL of anhydrous THF. A portion of the solids dissolved. After cooling this material to 0° C., a THF solution of dilithium salt of dimethylsilylbis(2-methylindene)$Et_2O$) (2.32 grams, 0.00576 mol; 17 mL THF) was added dropwise over 25 minutes. A dark orange solution resulted. No solids precipitated. The reaction was warmed to ambient temperature and stirred overnight. An aliquot of the clear solution was then stripped to an oily solid and redissolved in THF-$d_8$ for $^1H$ NMR. The NMR spectrum showed little or no racemic product.

Comparison Example 2

$ZrCl_4(THF)_2$ (2.17 g; 0.00575 mol) was placed in a 100 mL Schlenk flask with 13 mL of anhydrous toluene. This slurry was stirred with a magnetic stir bar and a solution of dilithium salt of dimethylsilylbis(2-methylindene)($Et_2O$) (2.32 grams, 0.00576 mol) in 16 mL of THF was added dropwise over 11 minutes. The reaction went clear and the solution became a dark orange. Toward the end of the addition the solution clouded and a precipitate began to form. The reaction was stirred overnight. The orange solids were then filtered on a 30 mL medium frit, washed with several mLs of toluene, and dried in vacuo. The yield of orange and brown solids was 1.03 grams (37.5%). After extracting this material into methylene chloride, the purified yield was determined to be 23%. A $^1H$ NMR spectrum in $CDCl_3$ showed pure product composed of approximately 93% racemic and 7% meso diasteriomers of dimethylsilylbis (2-methylindenyl)zirconium dichloride.

Example 5

$ZrCl_4$ (1.58 grams, 0.0678 moles) was slurried in 16 mL of anhydrous toluene. THF (1.17 grams, 0.0162 moles) was added dropwise. The dropping funnel was then charged with a solution of dilithium salt of dimethylsilylbis(2-methylindene)($Et_2O$) (2.74 grams, 0.00681 mol) and TMEDA (0.81 grams, 0.00697 mol) in 19 mL of anhydrous THF. After stirring for two hours, the solution of the dilithium salt of dimethylsilylbis(2-methylindene) (TMEDA) was added dropwise to the zirconium slurry. The solution cleared briefly during the addition and then an orange solid precipitated. The reaction was stirred overnight. The orange solids were then filtered on a medium frit, washed with 8 mL of toluene, and dried in vacuo. The yield of crude dimethylsilylbis(2-methylindenyl)zirconium dichloride was 1.26 grams (39%). The crude material provided a typical $^1H$ NMR spectrum in $CDCl_3$. The metallocene product was approximately 95% racemic and 5% meso. A purified yield was not determined.

Example 6

$ZrCl_4$ (3.04 grams, 0.0130 mol) was slurried in 13 mL of anhydrous toluene. TMEDA (1.57 grams, 0.0135 mol) was added dropwise. THF (8 mL) was then added. The slurry was stirred for 1.5 hours. The dilithium salt of dimethylsilylbisindene($Et_2O$) (4.85 grams, 0.0130 mol) was dissolved in 28 mL of anhydrous THF and then added dropwise to the zirconium slurry over 25 minutes. The solution cleared briefly during the addition and then an orange solid precipitated. The reaction was stirred overnight. The orange solids were then filtered on a coarse frit, washed with 5 mL of toluene and 5 mL of hexanes, and dried in vacuo. The yield of dimethylsilylbisindenylzirconium dichloride was 4.44 grams (76%). A sample was dissolved in $CDCl_3$ for $^1H$ NMR. The NMR spectrum showed pure racemic product.

Comparison Example 3

$ZrCl_4$ (3.03 grams, 0.0130 mol) was slurried in 13 mL of anhydrous toluene. THF (8 mL) was then added. A dropping funnel was charged with a solution of the dilithium salt of dimethylsilylbisindene ($Et_2O$) (4.85 grams, 0.0130 mol) in 28 mL of anhydrous THF. After stirring for one hour, the ligand solution was added dropwise to the zirconium slurry over 30 minutes. The solution cleared briefly during the addition and then, almost immediately, an orange solid precipitated. The reaction was stirred overnight. The orange solids were then filtered on a coarse frit, washed with 5 mL of toluene and 5 mL of hexanes, and dried in vacuo. The yield of dimethylsilylbisindenylzirconium dichloride was 4.13 grams (71%). A sample was dissolved in $CDCl_3$ for $^1H$ NMR. The NMR spectrum showed pure racemic product.

Example 7

Under a $N_2$ pad, $ZrCl_4$ (2.56 grams, 0.011 mol), 18 grams toluene solvent and TMEDA (1.32 grams, 0.0114 mol) in a 100 cc flask were stirred, heated up and held at 80°–90° C. for 1 hour. After cooling down, a mixture of THF (1.0 gram), dimethylsilylbisindenyl zirconium dichloride (0.04 gram), and toluene (4.0 grams) were added at 17° C. The dilithium salt of dimethylsilylbisindene-($Et_2O$) (22.33 grams, 0.01 mol) in THF solution (18 weight percent) in a dropping funnel was then fed continuously with the first half being fed for 30 minutes and the second half for 55 minutes at 18°–23° C. The reaction mixture was stirred at ~23° C. for 25 hours and then moved to a dry box. The resultant orange slurry was easily filtered (with a 60 mL 4–4.5 micron glass frit filter) and 7 grams of toluene were used to wash the wet cake. After being dried, 4.57 grams of orange product were obtained (~94% crude yield excluding the added dimethylsilylbisindenyl zirconium dichloride) based on dilithium salt of dimethylsilylbisindene-($Et_2O$). NMR showed that the sample of the crude product had 88% racemic and 12% meso isomers.

Example 8

$HfCl_4$-TMEDA adduct (2.50g, 5.73 mmol) was suspended in 20 mL of toluene and cooled to 0° C. The dilithium derivative of dimethylsilylbisindene (2.11 g, 5.64 mmol) was dissolved in 9.5 grams of 1,2-dimethoxyethane and added dropwise to the suspension of the hafnium tetrachloride adduct. The slurry which formed was allowed to warm to ambient room temperature and stir overnight. The solids were filtered easily on a coarse frit, washed with toluene, and dried in vacuo. The yield of yellow solids, (dimethylsilylbisindenylhafnium dichloride), was 2.53 grams or 68% (after subtracting the theoretical weight of byproduct LiCl).

Example 1 demonstrates that by using a diamine adduct in THF, racemic product was produced in contrast to Comparison Example 1 which produced little or no racemic product. Examples 2 to 6 demonstrate the improved yields obtained by using a mixed solvent in combination with the diamine adduct.

Example 7 demonstrates that an improved yield of an easily filterable product is obtained by preparing the diamine adduct at elevated temperatures and adding a small amount of product and THF to the adduct prior to the metallization reaction. Example 8 demonstrates that the process of this invention when conducted in a proper manner can provide excellent yields of bridged hafnium metallocenes.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended, formed in situ, or mixed with one or more other substances, components and/or ingredients in accordance with the present disclosure. The fact that the substance, component or ingredient may have lost its original identity through a chemical reaction or transformation during the course of such contacting, blending, formation in situ, or mixing operations is thus wholly immaterial for an accurate understanding and appreciation of this disclosure and the claims thereof.

Each and every patent or other publication referred to in any portion of this specification is incorporated in toto into this disclosure by reference for all purposes, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process for preparing a chiral metallocene, said process comprising mixing (i) a solution of a salt of an asymmetric bis(cyclopentadienyl)-moiety-containing ligand in whatever chemical form it exists while in said solution, with (ii) an organic liquid medium containing a solution or slurry of a chelate diamine adduct of a transition, lanthanide or actinide metal halide in whatever chemical form it exists while in said solution or slurry, at least 50 weight percent of the solvent or diluent of said solution of (i) being one or more liquid aliphatic or cycloaliphatic polyethers, and at least 50 weight percent of the solvent or diluent of said solution or slurry of (ii) being one or more liquid aliphatic, cycloaliphatic or aromatic hydrocarbons.

2. The process of claim 1 wherein said metal halide is a Group 4–6 metal halide.

3. The process of claim 1 wherein said solution of (i) is added to said solution or slurry of (ii).

4. The process of claim 3 wherein said chiral metallocene precipitates from the medium formed by adding (i) to (ii).

5. The process of claim 3 wherein said diamine adduct is formed at least in part from a diamine selected from the group consisting of N,N,N',N'-tetramethylethylenediamine and tetramethyldiaminomethane.

6. The process of claim 3 wherein said ligand comprises a pair of cyclopentadienyl moieties, at least one of which is asymmetric, which are joined by a silicon-containing bridging group.

7. The process of claim 6 wherein said bridging group contains 1–4 atoms and is selected from the group consisting of silanylene, silaalkylene, oxasilanylene and oxasilaalkylene.

8. The process of claim 7 wherein said bridging group is dimethylsilanylene.

9. The process of claim 7 wherein said chiral metallocene is racemic dimethylsilylbis(2-methylindenyl)zirconium dichloride.

10. The process of claim 7 wherein said chiral metallocene is racemic dimethylsilylbisindenylzirconium dichloride.

11. The process of claim 7 wherein said chiral metallocene is racemic dimethylsilylbis(2-methylindenyl) hafnium dichloride.

12. The process of claim 7 wherein said chiral metallocene is racemic dimethylsilylbisindenylhafium dichloride.

13. The process of claim 3 wherein said salt is an alkali metal salt or a magnesium halide salt.

14. The process of claim 3 wherein the solvent of said solution of (i) consists essentially of 1,2-dimethoxyethane, and wherein the solvent or diluent of said solution or slurry of (ii) consists essentially of one or more liquid mononuclear aromatic hydrocarbons having in the range of 6 to about 8 carbon atoms per molecule.

15. The process of claim 14 wherein said metal halide is a hafnium tetrahalide.

16. The process of claim 3 wherein said metal halide is a zirconium tetrahalide.

17. A process for preparing a chiral metallocene, said process comprising adding (i) a solution of an alkali metal salt of an asymmetric bis(cyclopentadienyl)-moiety-containing ligand in whatever chemical form it exists while in said solution, to (ii) an solution or slurry of a chelate diamine adduct of a Group 4 metal halide in whatever chemical form the adduct exists while in said solution or slurry, at least 50 weight percent of the solvent of said solution of (i) being one or more liquid aliphatic or cycloaliphatic diethers, and at least 50 weight percent of the liquid solvent or diluent of said solution or slurry of (ii) being one or more liquid aliphatic, cycloaliphatic or aromatic hydrocarbons.

18. The process of claim 17 wherein said solution of an alkali metal salt of an asymmetric bis(cyclopentadienyl)-moiety-containing ligand is a solution of a lithium salt of an asymmetric bis(cyclopentadienyl)-moiety-containing ligand.

19. The process of claim 18 wherein the chelate diamine is N,N,N',N'-tetramethylethylenediamine and tetramethyldiaminomethane, and the Group 4 metal halide is zirconium tetrachloride or hafnium tetrachloride.

20. The process of claim 19 wherein said salt is the dilithium salt of a ligand comprising a pair of cyclopentadienyl moieties, at least one of which is asymmetric, which are joined by a silicon-containing bridging group that contains from 1 to 4 atoms and is selected from the group consisting of silanylene, silaalkylene, oxasilanylene and oxasilaalkylene.

21. The process of claim 20 wherein the Group 4 metal halide is hafnium tetrachloride, wherein said diether consists essentially of 1,2-dimethoxyethane, and wherein said bridging group is a silanylene bridging group.

22. The process of claim 21 wherein said ligand is dimethylsilylbisindene and said chiral metallocene is racemic dimethylsilylbisindenylzirconium dichloride, and wherein the solvent or diluent of said solution or slurry of (ii) consists essentially of one or more liquid mononuclear aromatic hydrocarbons having in the range of 6 to about 8 carbon atoms per molecule.

23. The process of claim 21 wherein the liquid solvent or diluent of said solution or slurry of (ii) consists essentially of toluene.

* * * * *